(12) United States Patent
Milz et al.

(10) Patent No.: US 9,101,494 B2
(45) Date of Patent: Aug. 11, 2015

(54) INSERTION INSTRUMENT FOR INTERVERTEBRAL IMPLANTS

(71) Applicant: Stryker Spine, Cestas (FR)

(72) Inventors: Bryan D. Milz, Florida, NY (US); Robert Cipoletti, Pompton Plains, NJ (US); Thomas A. Alheidt, Sussex, NJ (US)

(73) Assignee: Stryker Spine (FR)

( * ) Notice: Subject to any disclaimer, the term of this patent is extended or adjusted under 35 U.S.C. 154(b) by 0 days.

(21) Appl. No.: 14/321,258

(22) Filed: Jul. 1, 2014

(65) Prior Publication Data

US 2014/0316477 A1 Oct. 23, 2014

Related U.S. Application Data

(63) Continuation of application No. 12/228,251, filed on Aug. 11, 2008, now Pat. No. 8,801,758.

(60) Provisional application No. 60/964,624, filed on Aug. 13, 2007.

(51) Int. Cl.
*A61B 17/88* (2006.01)
*A61F 2/46* (2006.01)
(Continued)

(52) U.S. Cl.
CPC ............... *A61F 2/4611* (2013.01); *A61B 17/56* (2013.01); *A61B 17/88* (2013.01); *A61B 17/885* (2013.01);
(Continued)

(58) Field of Classification Search
CPC .. A61B 17/56; A61B 2017/564; A61B 17/88; A61B 17/885; A61B 17/8872; A61B 17/92; A61B 2017/0256; A61F 2/46; A61F 2/4603; A61F 2/4611; A61F 2002/4627; A61F 2002/4628

USPC ................. 606/86 A, 86 B, 90, 99, 105, 279; 623/17.11, 17.16

See application file for complete search history.

(56) References Cited

U.S. PATENT DOCUMENTS 3,486,505 A 12/1969 Morrison
5,423,825 A 6/1995 Levine
(Continued)

FOREIGN PATENT DOCUMENTS

EP 1323396 7/2003
WO 2007055819 5/2007

OTHER PUBLICATIONS

International Search Report for PCT/US2008/009574 dated Dec. 3, 2008.
(Continued)

*Primary Examiner* — Larry E Waggle, Jr.
(74) *Attorney, Agent, or Firm* — Lerner, David, Littenberg, Krumholz & Mentlik, LLP

(57) ABSTRACT

An insertion tool for positioning intervertebral spacers into disc spaces. The insertion tool has a proximal end and a distal end, a T-handle secured to the proximal end and a pair of alignment rails extending to the distal end. The insertion tool includes a handle secured to the proximal end of the guide rails, and a shaft that extends through the handle, whereby the shaft has a threaded portion that extends to the T-handle. The insertion tool also includes a blocker that is secured to the distal end of the shaft. The blocker includes stop arms that guide the blocker through the guide rails and toward the distal end of the shaft. The blocker may be provided in a plurality of different sizes corresponding to the sizes of the implants to be inserted into a disc space. A lock is provided for locking the implant to the shaft.

18 Claims, 19 Drawing Sheets

(51) Int. Cl.
*A61B 17/56* (2006.01)
*A61B 17/92* (2006.01)
*A61B 17/02* (2006.01)
*A61F 2/30* (2006.01)

(52) U.S. Cl.
CPC ............... *A61B 17/8872* (2013.01); *A61F 2/46* (2013.01); *A61F 2/4603* (2013.01); *A61B 17/92* (2013.01); *A61B 2017/0256* (2013.01); *A61B 2017/564* (2013.01); *A61F 2002/30484* (2013.01); *A61F 2002/30553* (2013.01); *A61F 2002/30616* (2013.01); *A61F 2002/30617* (2013.01); *A61F 2002/4627* (2013.01); *A61F 2002/4628* (2013.01); *A61F 2220/0025* (2013.01); *A61F 2250/0008* (2013.01); *A61F 2250/0097* (2013.01)

(56) References Cited

U.S. PATENT DOCUMENTS

| | | |
|---|---|---|
| 5,431,658 A | 7/1995 | Moskovich |
| 5,885,299 A | 3/1999 | Winslow et al. |
| 5,954,727 A | 9/1999 | Collazo |
| 6,004,326 A | 12/1999 | Castro et al. |
| 6,478,800 B1 | 11/2002 | Fraser et al. |
| 6,652,533 B2 | 11/2003 | O'Neil |
| 6,755,841 B2 | 6/2004 | Fraser et al. |
| 7,118,580 B1 | 10/2006 | Beyersdorff et al. |
| 7,625,379 B2 | 12/2009 | Puno et al. |
| 7,722,622 B2 | 5/2010 | Evans et al. |
| 8,486,081 B2 | 7/2013 | Parsons et al. |
| 2002/0116009 A1* | 8/2002 | Fraser et al. .................. 606/99 |
| 2003/0229355 A1 | 12/2003 | Keller |
| 2004/0162617 A1 | 8/2004 | Zucherman et al. |
| 2004/0181231 A1 | 9/2004 | Emstad et al. |
| 2004/0220582 A1 | 11/2004 | Keller |
| 2004/0225295 A1 | 11/2004 | Zubok et al. |
| 2005/0015094 A1 | 1/2005 | Keller |
| 2005/0021042 A1 | 1/2005 | Marnay et al. |
| 2005/0027300 A1 | 2/2005 | Hawkins et al. |
| 2005/0055095 A1 | 3/2005 | Errico et al. |
| 2005/0119665 A1 | 6/2005 | Keller |
| 2005/0143747 A1 | 6/2005 | Zubok et al. |
| 2005/0165408 A1 | 7/2005 | Puno et al. |
| 2005/0203538 A1 | 9/2005 | Lo et al. |
| 2006/0004376 A1 | 1/2006 | Shipp et al. |
| 2006/0030856 A1 | 2/2006 | Drewry et al. |
| 2006/0058808 A1 | 3/2006 | Schneid |
| 2006/0089656 A1 | 4/2006 | Allard et al. |
| 2006/0095043 A1 | 5/2006 | Martz et al. |
| 2006/0149284 A1 | 7/2006 | McCormack et al. |
| 2006/0167461 A1 | 7/2006 | Hawkins et al. |
| 2006/0200166 A1 | 9/2006 | Hanson et al. |
| 2006/0200241 A1 | 9/2006 | Rothman et al. |
| 2006/0229627 A1 | 10/2006 | Hunt et al. |
| 2006/0241641 A1 | 10/2006 | Albans et al. |
| 2006/0241764 A1 | 10/2006 | Michelson |
| 2006/0247655 A1 | 11/2006 | Francis et al. |
| 2006/0287728 A1 | 12/2006 | Mokhtar et al. |
| 2006/0293684 A1 | 12/2006 | Shluzas et al. |
| 2007/0010826 A1 | 1/2007 | Rhoda et al. |
| 2007/0016218 A1 | 1/2007 | Winslow et al. |
| 2007/0050031 A1 | 3/2007 | Khosrowshahi |
| 2007/0055241 A1 | 3/2007 | Matthis et al. |
| 2007/0073311 A1 | 3/2007 | Williams et al. |
| 2007/0073405 A1 | 3/2007 | Verhulst et al. |
| 2007/0093849 A1 | 4/2007 | Jones et al. |
| 2007/0093850 A1 | 4/2007 | Harris et al. |
| 2007/0093897 A1 | 4/2007 | Gerbec et al. |
| 2007/0100454 A1 | 5/2007 | Burgess et al. |
| 2007/0100456 A1 | 5/2007 | Dooris et al. |
| 2007/0185375 A1* | 8/2007 | Stad et al. .................. 600/101 |
| 2008/0177275 A1 | 7/2008 | Wing et al. |
| 2009/0030422 A1* | 1/2009 | Parsons et al. .................. 606/99 |

OTHER PUBLICATIONS

Written Opinion for PCT/US2008/009574 dated Dec. 3, 2008.

* cited by examiner

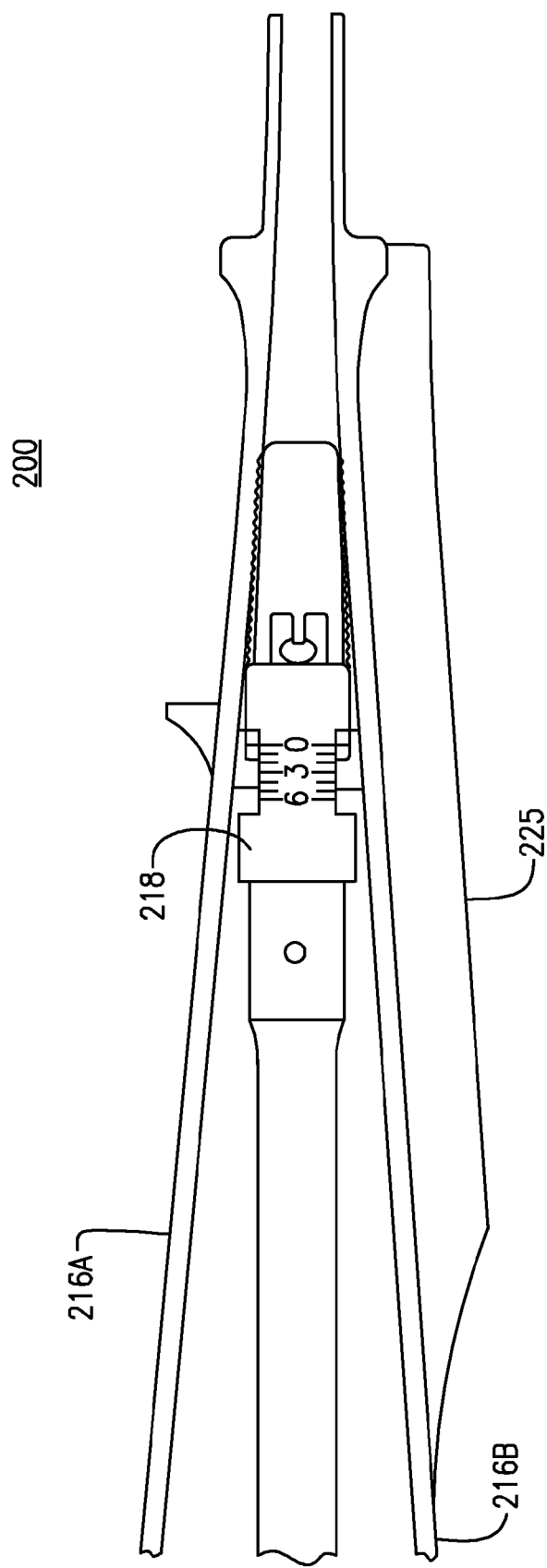

INSERTION INSTRUMENT FOR INTERVERTEBRAL IMPLANTS

CROSS-REFERENCE TO RELATED APPLICATIONS

This application is a continuation of U.S. patent application Ser. No. 12/228,251, filed on Aug. 11, 2008, which claims the benefit of the filing date of U.S. Provisional Patent Application No. 60/964,624 filed Aug. 13, 2007, the disclosures of which are hereby incorporated herein by reference.

FIELD OF THE INVENTION

The present invention relates to spinal stabilization and more particularly relates to systems and tools for inserting implants into intervertebral disc spaces.

BACKGROUND OF THE INVENTION

There have been many recent developments in the field of spinal stabilization. In some instances, plates are used to stabilize spinal segments. In other instances, however, pedicle screws and stabilizing rods are utilized for stabilizing spinal segments. More recently, there have been a number of advances using implants placed into disc spaces between vertebral bodies. These advances also involve the use of tools for preparing the disc space and inserting the implants.

In spite of the above advances, there remains a need for improved methods and tooling for stabilizing spinal segments.

SUMMARY OF THE INVENTION

In certain preferred embodiments, the present invention provides an insertion tool for positioning intervertebral spacers into disc spaces. In certain preferred embodiments, the present invention discloses an insertion tool having a proximal end and a distal end, a T-handle secured to the proximal end and a pair of alignment rails extending to the distal end. The insertion tool includes a handle secured to the proximal end of the guide rails, and a shaft that extends through the handle, whereby the shaft has a threaded portion that extends to the T-handle. The insertion tool also includes a blocker that is secured to the distal end of the shaft. The blocker includes stop arms that guide the blocker through the guide rails and toward the distal end of the shaft. The blocker may be provided in a plurality of different sizes, in response to the size of an implant to be inserted into a disc space. An implant may be secured to the blocker and advanced toward the distal end of the tool using the shaft and the blocker.

In certain preferred embodiments, the shaft has a bore extending from the proximal end to the distal end thereof. An internal locking shaft may be extendible through the bore of the shaft for selectively securing the implant to the blocker.

In one aspect the present invention provides an intervertebral implant insertion instrument having a first handle having a first end and a second end. A second handle is located towards the first end and connected to the first handle. A pair of rails is attached to the second end of the first handle. A shaft having a third end and a fourth end threadably engages the first handle. A blocker is attached to the fourth end of the shaft. The blocker is adapted to accept a fifth intervertebral implant such that when the fifth intervertebral implant is advanced towards the vertebrae the rails do not contact the fifth implant.

In another aspect the present invention teaches a method of implanting an intervertebral implant. The method includes the steps of: inserting a distal end of an intervertebral implant insertion instrument between two vertebrae, the implant insertion instrument including a first handle and a second handle; attaching a blocker to the implant insertion instrument; attaching an implant to the blocker, the implant having a top and a bottom surface; and sliding the implant along a guide path on the implant insertion instrument and between the vertebrae without the top and surfaces of the implant being contacted by the implant insertion instrument.

These and other preferred embodiments of the present invention will be described in more detail below.

BRIEF DESCRIPTION OF THE DRAWINGS

FIG. 18C shows a side view of the insertion tool shown in FIGS. 18A-18B.

DETAILED DESCRIPTION

Figure 1A:
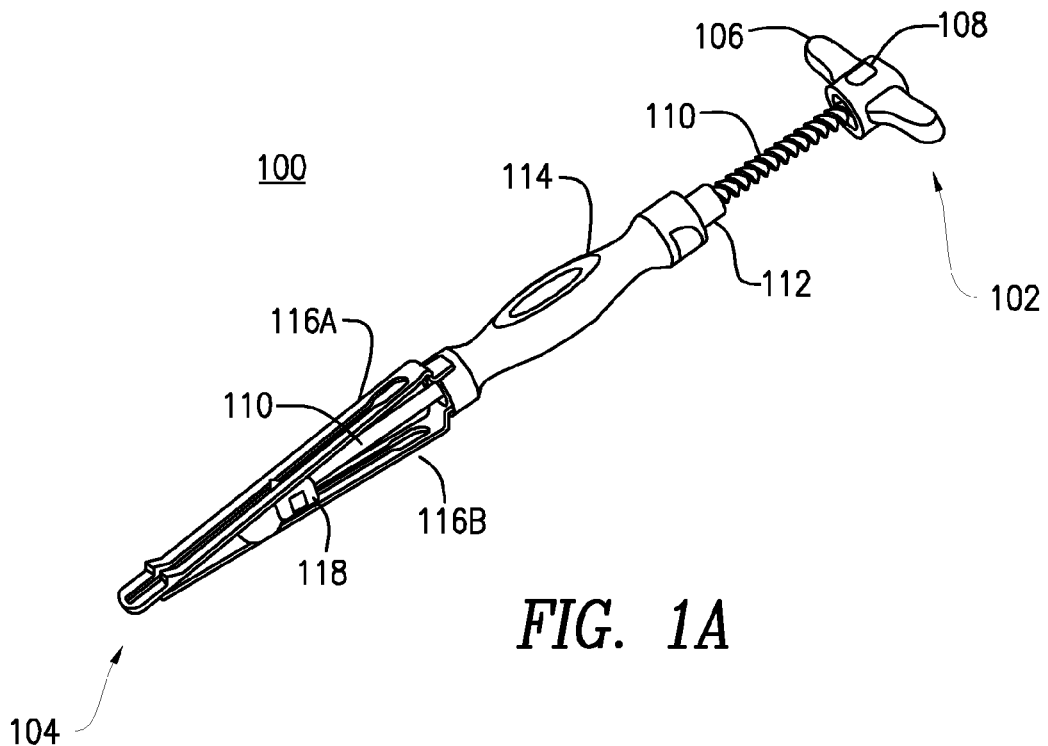
FIGS. 1A and 1B show perspective views of an insertion tool for an intervertebral implant, in accordance with certain preferred embodiments of the present invention.
Figure 1B:
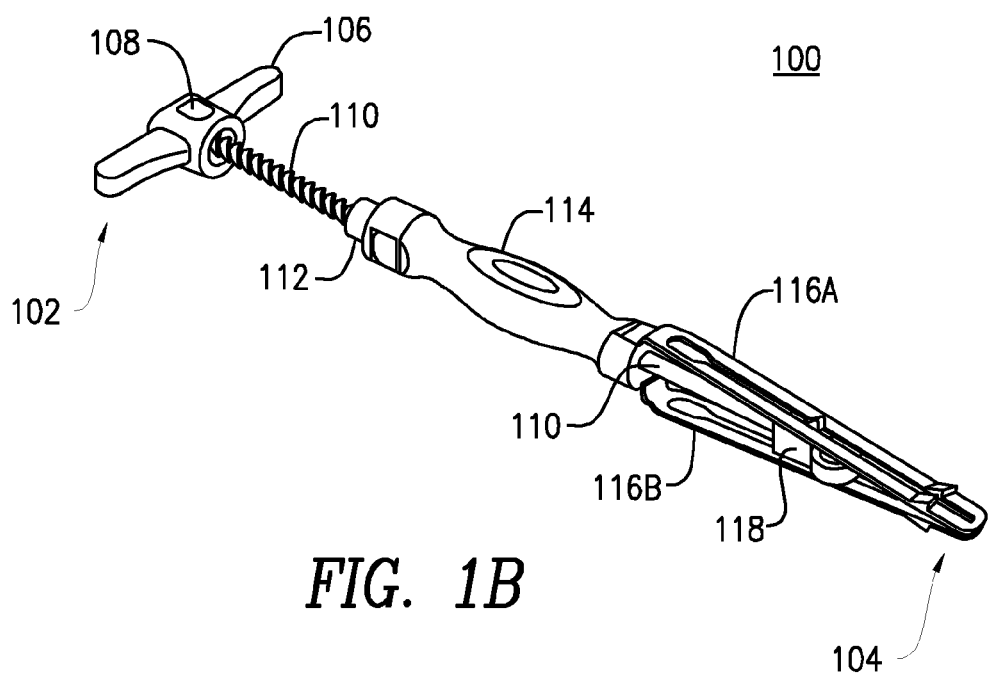

Referring to FIGS. 1A and 1B, in one preferred embodiments of the present invention, an insertion tool 100 has a proximal end 102 and a distal end 104. The insertion tool 100 includes a rotatable T-handle 106 having an implant lock 108 movable between a locked position and an unlocked position. The T-handle 106 is coupled with a shaft 110 that extends from the T-handle, through a sleeve 112 and a handle 114, and toward the distal end 104 of the insertion tool 100. The handle 114 that is located between the sleeve 112 and a pair of guide rails 116A, 116B that are pivotally connected to the distal end of the handle. As a result of the pivot connections, the distal ends of the guide rails are able to move away from one another for distracting a disc space. The inserter 100 also includes blocker 118 that may be coupled with a distal end of the shaft 110.

The proximal end of the shaft 110 has external threads that mesh with the sleeve 112 for moving the shaft proximally or distally relative to the sleeve. The distal end of the shaft 110 is non-threaded. As will be described in more detail below, the shaft 110 has a central bore that is adapted to receive an internal locking shaft used to couple an implant with a distal end of the insertion tool.

Figure 2:
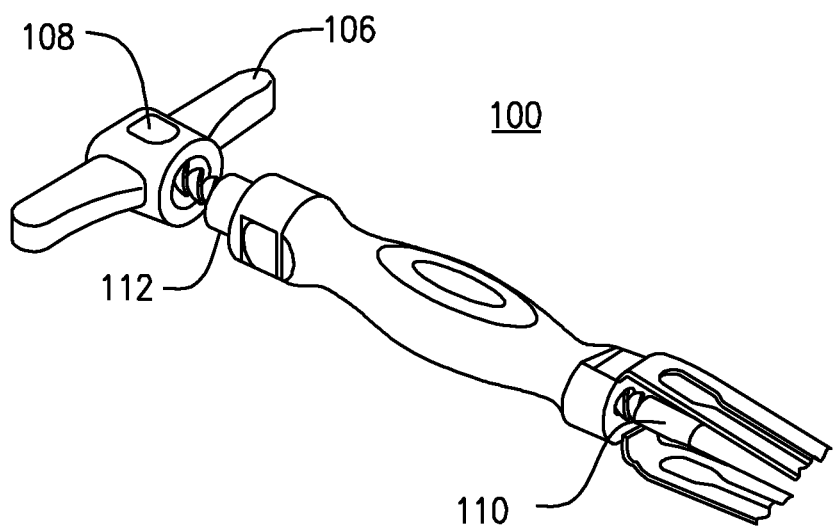
FIG. 2 shows a proximal end of the insertion tool shown in FIGS. 1A and 1B.

FIG. 2 shows the T-handle 106 connected with the threaded portion of the shaft at the proximal end of the shaft. The T-handled 106 may be rotated in a first direction for advancing the shaft 110 toward the distal end of the tool, and in a second opposite direction for retracting the shaft toward the proximal end of the tool. The T-handle 106 may be rotated in the first direction until the sleeve 112 is fully received within the T-handle as shown in FIG. 3.

Figure 3:
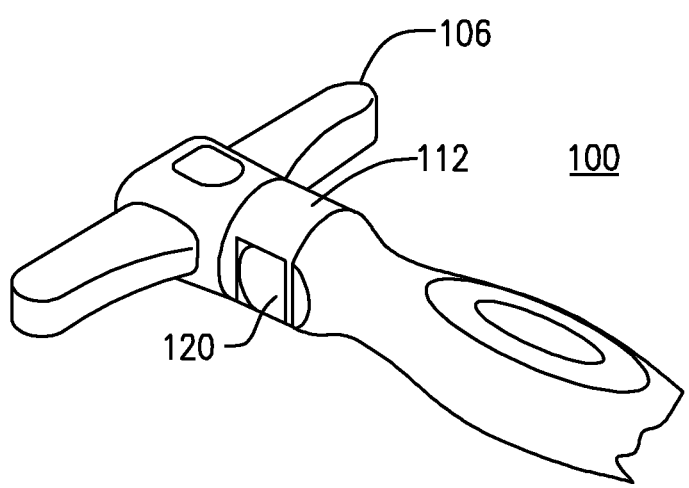
FIG. 3 shows another view of the proximal end of the insertion tool shown in FIG. 2 including a T-handle, a sleeve and a handle.

Referring to FIG. 3, the sleeve 112 includes a depressible button 120 that may be depressed when it is desirable to disengage the sleeve from the threads on the shaft 110 for quickly advancing the T-handle 106 and the shaft 110 toward the distal end of the insertion tool 100.

Figure 4A:
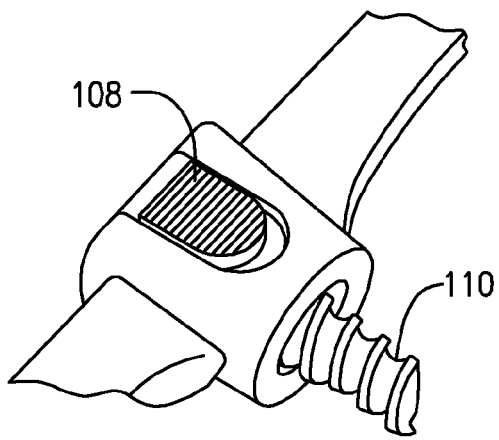
FIGS. 4A and 4B show an expanded view of the T-handle at the proximal end of the insertion tool shown in FIG. 3.
Figure 4B:
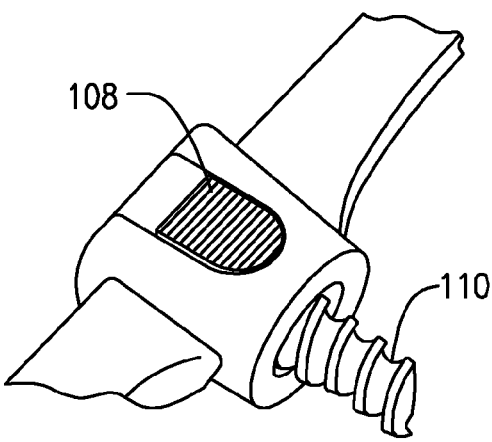

FIGS. 4A and 4B show an implant lock 108 that is used for securing an implant to a distal end of the shaft 110. FIG. 4A shows the implant lock 108 in the unlocked position. FIG. 4B shows the implant lock 108 after it has been advanced into the locked position. As noted above, the implant lock 108 is moved between the unlocked and locked positions for selectively securing an implant to a distal end of the shaft 110.

Figure 5:
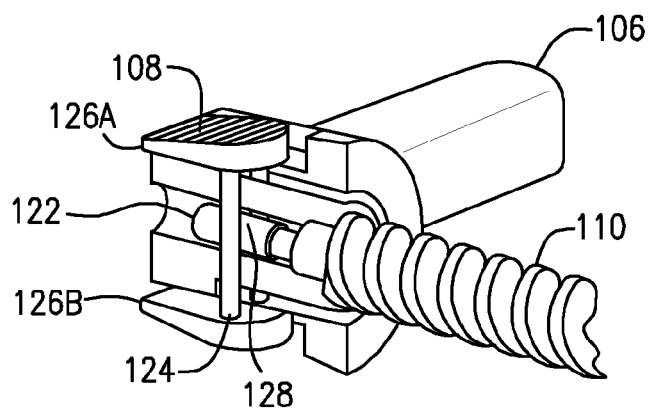
FIG. 5 shows a cross-sectional view of the T-handle at the proximal end of the insertion tool shown in FIG. 3.

FIG. 5 shows a partial cross-sectional view of the insertion tool including the T-handle 106 connected with a proximal end of the shaft 110. As shown in FIG. 5, the shaft 110 is hollow and includes an internal locking shaft 122 provided therein. The internal locking shaft 122 is coupled with the implant lock 108 and is slideable along the longitudinal axis of the shaft 110. The implant lock 108 includes a pair of pins 124 that extend between an upper tab 126A and a lower tab 126B. The pins 124 engage an undercut 128 formed adjacent the proximal end of the internal locking shaft. The T-handle 106 is secured to the proximal end of the shaft 110 so that the T-handle and the shaft rotate together. The internal locking shaft 122 is not designed to rotate with the T-handle 106. The internal locking shaft 122 is designed to be selectively moved along the longitudinal axis of the shaft 110 for moving the internal locking shaft between an advanced locking position and a retracted unlocking position. As the T-handle 106 is rotated, the pins 124 of the implant lock 108 rotate about the undercut 128 on the internal locking shaft 122.

Figure 6A:
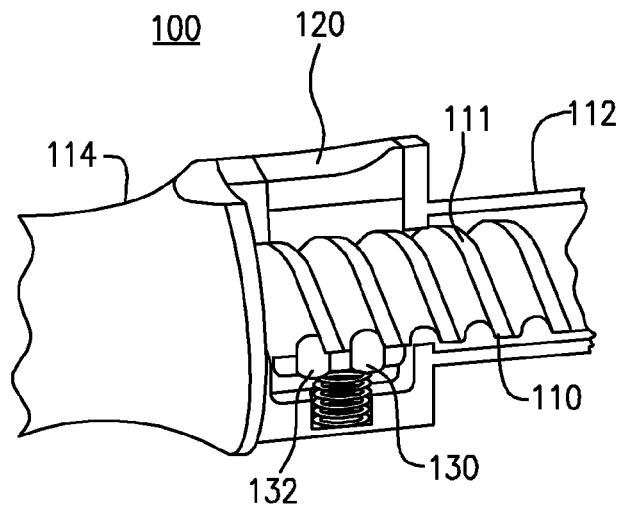
FIGS. 6A and 6B show a cross-sectional view of the sleeve a portion of the insertion tool shown in FIG. 3.
Figure 6B:
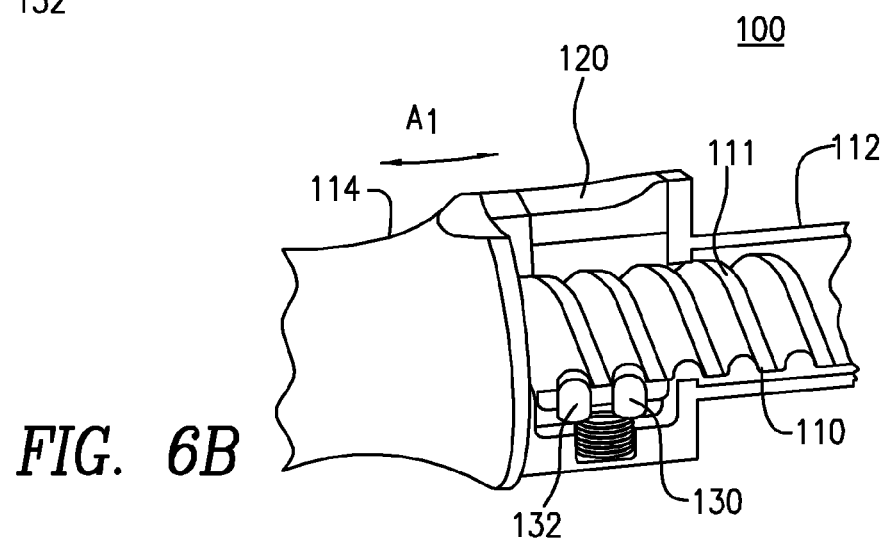

FIGS. 6A and 6B show a partial cross-sectional view of the insertion tool 100 including the depressible threaded shaft button 120. In the normal position shown in FIG. 6A, the sleeve 112 is coupled with the threaded section of the shaft 110 via spring element 130 and nubs 132, the latter elements engaging the threads 111 of the shaft 110. As the shaft 110 is rotated, the sleeve 112 may be advanced toward the proximal or distal end of the tool.

FIG. 6B shows the depressible threaded shaft button 120 after it has been depressed. As a result of the depression of the threaded shaft button 120, the spring element 130 is compressed so that the nubs 132 are disengaged from the threads 111. As a result, the sleeve 112 may be rapidly advanced in either direction along the longitudinal axis $A_1$ of the shaft 110. For example, the button 120 may be depressed to quickly advance the distal end of the shaft 110 toward the distal end of the instrument 100.

Figure 6C:
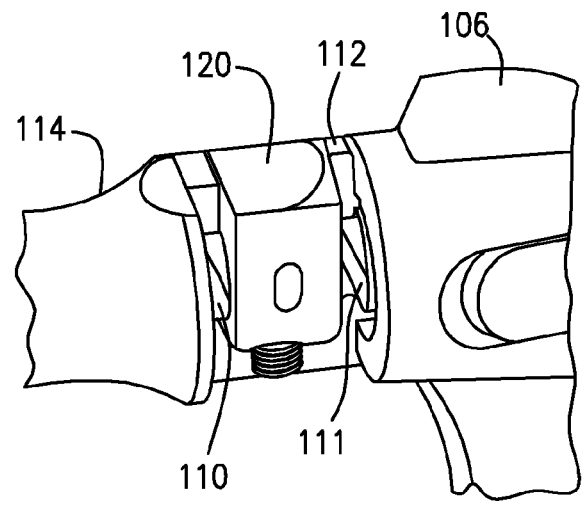
FIG. 6C shows another cross-sectional view of the sleeve portion of the insertion tool shown in FIG. 3.

FIG. 6C shows the depressible threaded shaft button 120 provided on the sleeve 112 and disposed between the T-handle 106 and the handle 114. When the button 120 is depressed, the sleeve 112 and the handle 114 may be quickly slid toward the distal end of the insertion instrument. When the depressible button 120 is released, and allowed to return to its normal position shown in FIG. 6C, the sleeve 112 is reengaged with the threads 111 on the shaft 110 and may only be advanced further by rotating the T-handle 106. At this point, the sleeve 112 is reengaged with the threaded shaft.

Figure 7A:
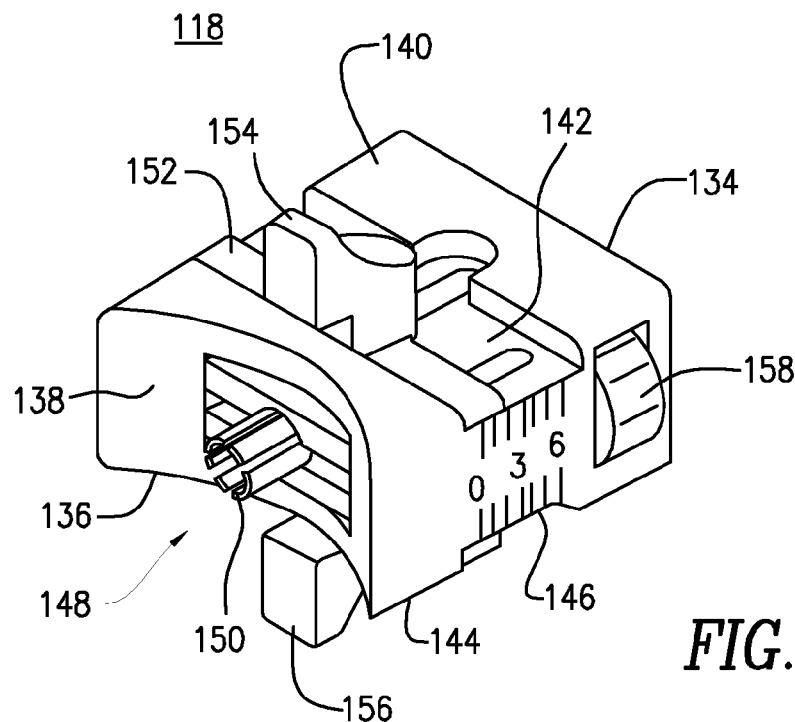
FIGS. 7A-7C show a blocker used in conjunction with the insertion tool shown in FIGS. 1A and 1B, in accordance with certain preferred embodiments of the present invention.
Figure 7B:
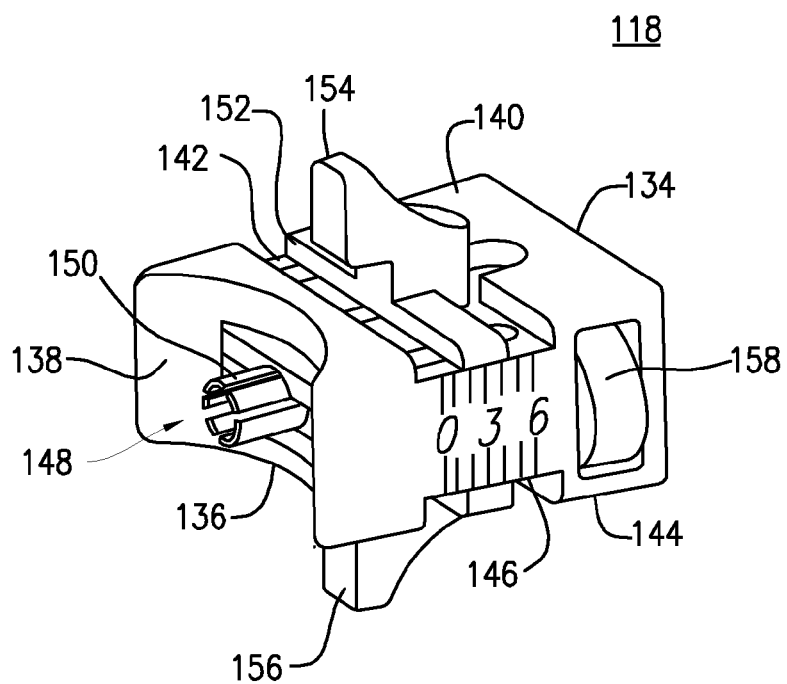
Figure 7C:
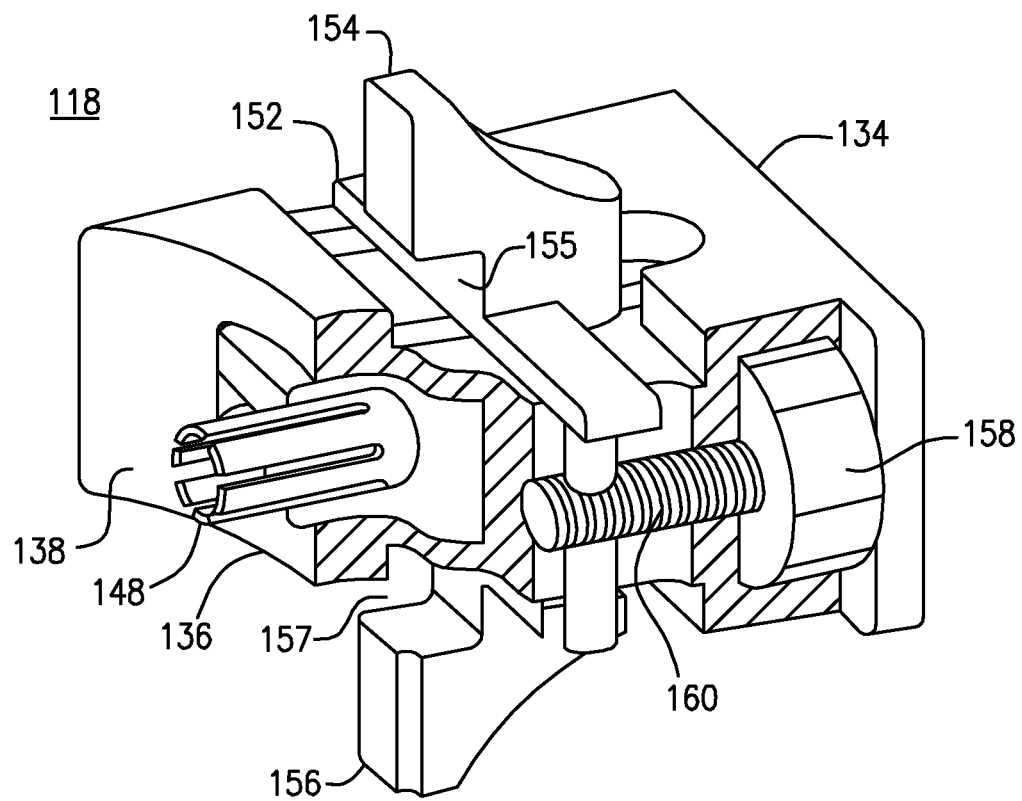

FIGS. 7A, 7B and 7C show a blocker 118, in accordance with certain preferred embodiments of the present invention. The blocker 118 is preferably attached to the distal end of the shaft 100. The blocker 118 includes a proximal end 134 and a distal end 136 having a concave face 138 adapted to seat an implant. The blocker 118 includes a top surface 140 having a first depression 142 formed therein and a bottom surface 144 having a second depression 146 formed therein. The blocker 118 includes a spring collet 148 projecting from the concave face 138. The spring collet 148 includes a plurality of spaced fingers 150 that are compressible toward one another. The fingers 150 may also be flexed away from one another due to advancement of the internal locking shaft [not shown] toward the distal end of the tool.

The blocker 118 also includes an offset element 152 including a first stop arm 154 projecting above the top surface 140. The first stop arm 154 has an undercut 155 not shown in FIGS. 7A, 7B shown in FIG. 7C. The blocker 118 includes a second stop arm 156 projecting below the bottom surface 144. The second stop arm also has an undercut 157.

The blocker 118 also includes an adjustment knob 158 that may be engaged for moving the stop arms 154, 156 between the proximal and distal ends thereof. The adjustment knob 158 enables the blocker 118 to be set at different offset distances from 0 MM to 6 MM so that the depth of the implant from an outer edge of an intervertebral disc space may be set. FIG. 7C shows a cross-sectional view of the blocker 118 shown in FIGS. 7A and 7B. The blocker 118 includes proximal end 134 and distal end 136 including concave face 138. The spring collet 148 extends from the concave face 138. The blocker 118 includes offset adjustment elements 152 that may be moved between the proximal and distal ends of the blocker by rotating the thumb screw 158. As the thumb screw 158 is rotated, a threaded shaft 160 attached to the thumb screw 158 is also rotated. The threaded shaft 160 engages the adjustment element 158, which, in turn, is connected with the stop arms 154 and 156.

Figure 8C:
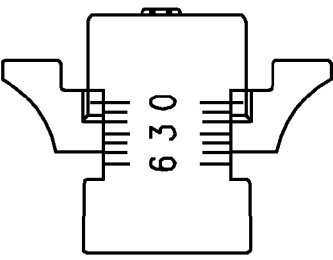
FIGS. 8A-8F show a plurality of blockers having different sizes, in accordance with certain preferred embodiments of the present invention.
Figure 8B:
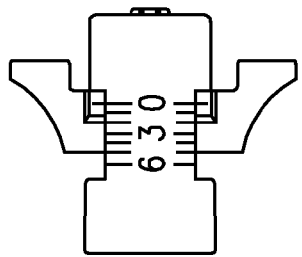
Figure 8A:
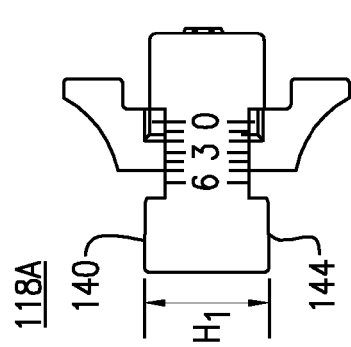
Figure 8F:
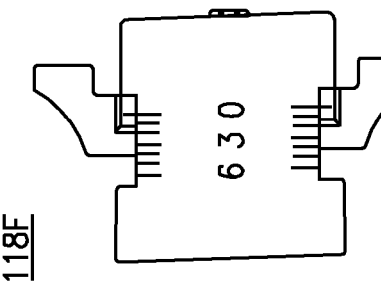
Figure 8E:
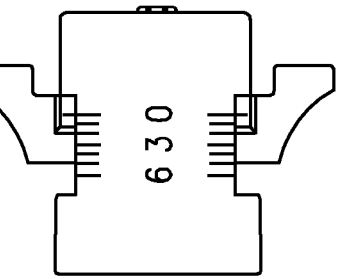
Figure 8D:
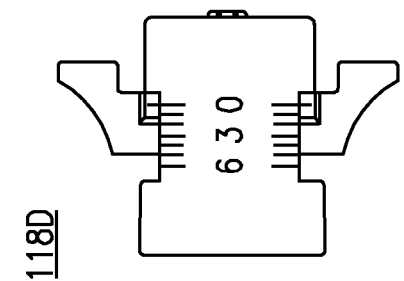

Referring to FIGS. 8A-8F, in certain preferred embodiments of the present invention, a plurality of blockers 118 are provided. Each blocker has a height that extends between the top surface 140 and the bottom surface 144 thereof. FIGS. 8A-8F show a plurality of blockers having different heights. For example, the blocker 118B shown in FIG. 8B has a greater height than the blocker 118A shown in FIG. 8A. In turn, the blocker 118C shown in FIG. 8C has a greater height than the blocker 118B shown in FIG. 8B. Each blocker has a size or height that the specifically designed to accommodate a particular implant height. In the particular preferred embodiment shown in FIGS. 8A-8F, the blockers are associated with implants having the following heights: blocker 118A in FIG. 8A is for a 10 MM implant, blocker 118B in FIG. 8B is for a 12 MM implant, blocker 118C in FIG. 8C is for a 14 MM implant, blocker 118D in FIG. 8D is for a 16 MM implant, blocker 118E in FIG. 8E is for an 18 MM implant, and blocker 118F in FIG. 8F is for a 20 MM implant.

Figure 9:
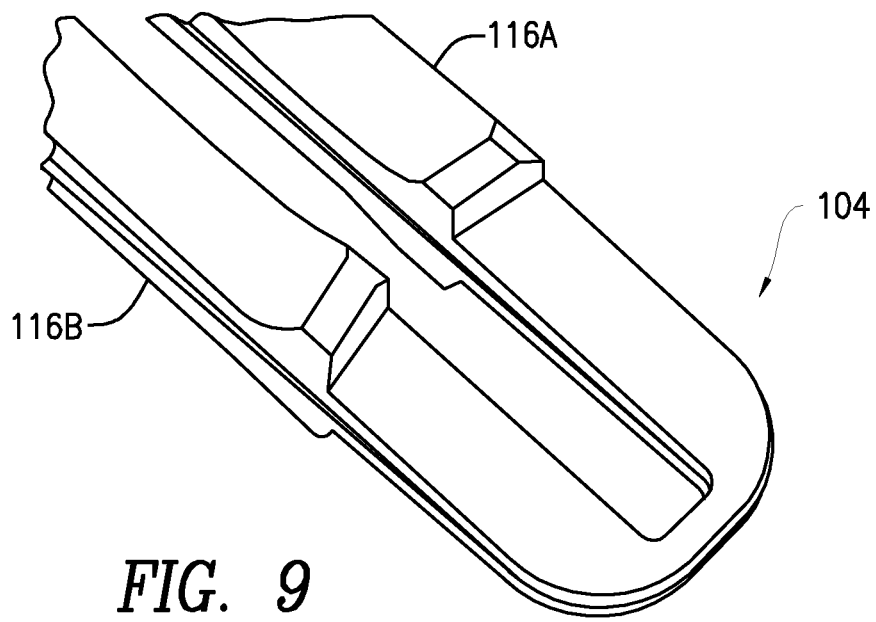
FIG. 9 shows a distal end of the insertion tool shown in FIGS. 1A and 1B.
Figure 10:
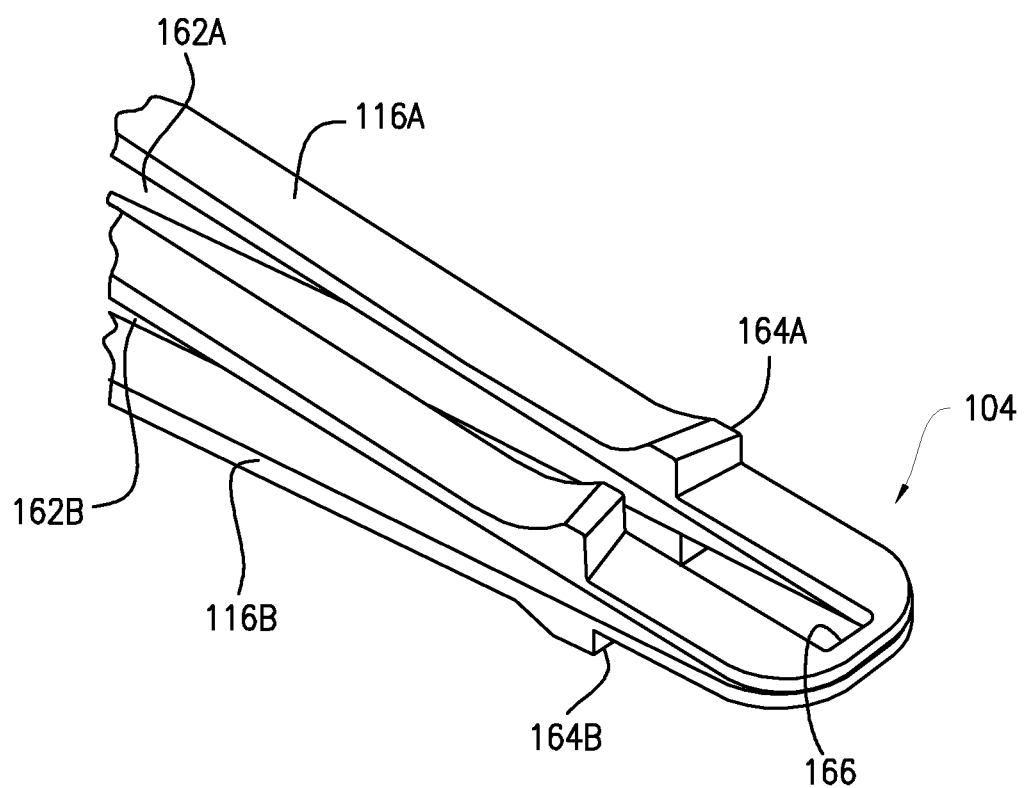
FIG. 10 shows another view of the distal end of the insertion tool shown in FIG. 9.

FIG. 9 shows the distal end 104 of the insertion instrument 100, in accordance with certain preferred embodiments of the present invention. The distal end of the insertion instrument preferably includes a first guide rail 116A and a second guide rail 116B. Referring to FIG. 10, the first guide rail 116A desirably includes a first slot 162A that extends to the distal end 104 of the instrument. The second guide rail 116B desirably includes a second slot 162B that also extends toward the distal end of the insertion instrument. Each of the guide rails 116A, 116B includes a respective vertebral body stopper 164A, 164B that prevents over insertion of the rails into a disc space between vertebral bodies.

The slots 162A, 162B in the respective rails 116A, 116B terminate before the distal-most end of the insertion tool so that the slots are closed at their distal ends 166. The distal ends 166 of the slots 162A, 162B are adapted to halt advancement of the blocker beyond the distal end of the tool. The slots 162A, 162B are designed to receive the stop arms of the blocker (shown in FIG. 7C) for guiding the blocker towards the distal end of the insertion tool. The guiding of the stop arms of the blocker in the slots 162A, 162B of the respective rails 116A, 116B provide stabilization for the blocker as the blocker is moved toward the distal end of the insertion tool.

Figure 11A:
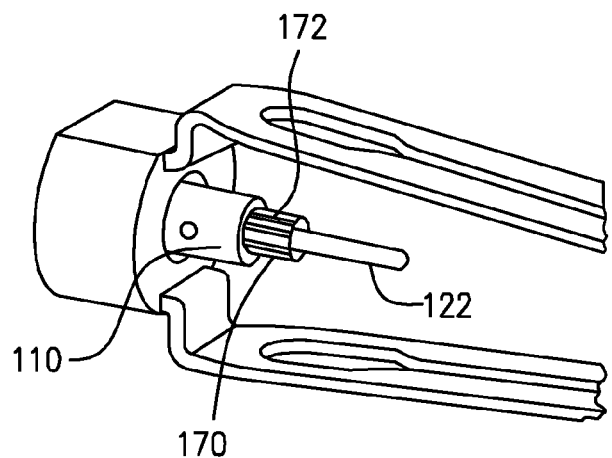
FIGS. 11A-11C show a method of assembling the blocker of FIG. 7A and an implant with the insertion tool of FIGS. 1A and 1B, in accordance with certain preferred embodiments of the present invention.
Figure 11B:
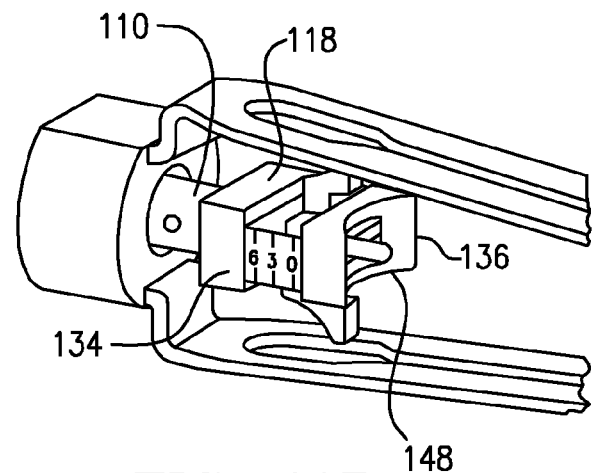

FIG. 11A shows the distal end of shaft 110, which has a shaft spring collet 170 projecting therefrom. The shaft spring collet 170 includes a plurality of spaced fingers 172 that are adapted to flex relative to one another. The fingers may be compressed toward one another or expanded away from one another in response to forces. FIG. 11A also shows a distal end of the internal locking shaft 122, which projects from the shaft spring collet 170 and the distal end of the shaft 110. Referring to FIG. 11B, one of the blockers 118 shown and described above may be secured to the distal end of the shaft 110. In certain preferred embodiments, the securing may be accomplished by inserting the shaft spring collet 170 into a bore extending through blocker 118. The bore preferably extends from a proximal end to a distal end of the blocker. The internal locking shaft 122 may then be advanced to expand the fingers 172 of the shaft spring collet 170 to secure the blocker to the distal end of the shaft 110.

Figure 11C:
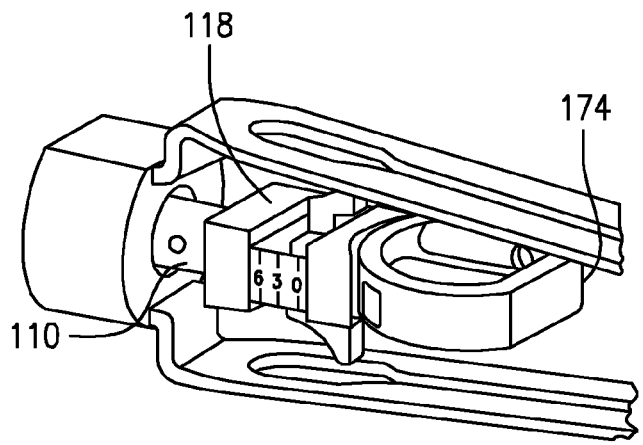

Referring to FIG. 11C, after the blocker 118 is secured to the distal end of the shaft 110, an implant 174 may be secured to the blocker 118. The blocker spring collet 148 and the internal locking shaft 122 are preferably inserted into a bore at a trailing end of the implant 174 for securing the implant with the blocker 118.

Figure 12A:
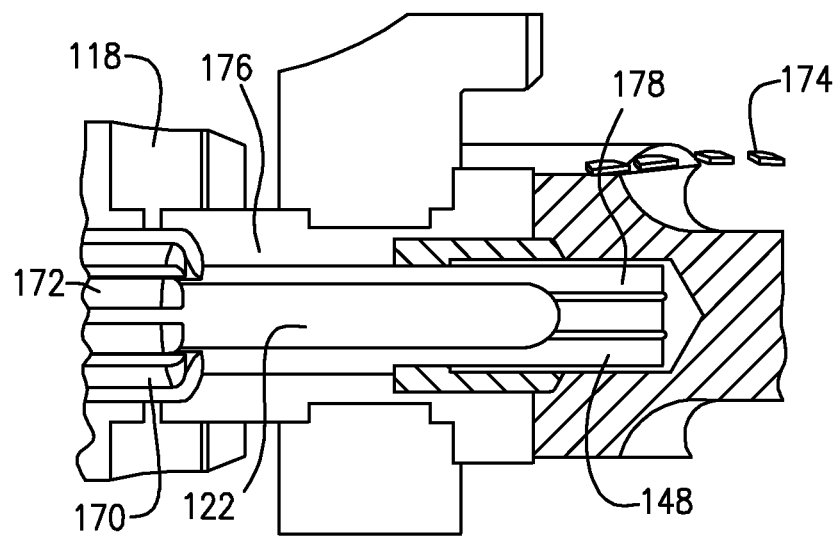
FIGS. 12A and 12B show a method of assembling an implant with the blocker of FIG. 7A and the insertion tool of FIGS. 1A and 1B, in accordance with certain preferred embodiments of the present invention.
Figure 12B:
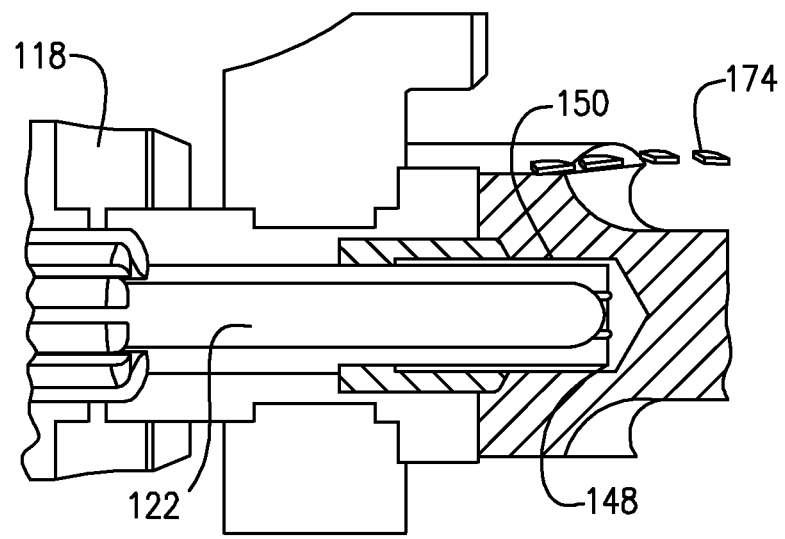

FIGS. 12A and 12B show the implant 174 being secured to the distal end of the blocker 118. Referring to FIGS. 11A and 12A, in order to secure the blocker 118 with the distal end of the shaft 110, the shaft spring collet 170 and the distal end of the internal locking shaft 122 are inserted into the bore 176 extending through the blocker 118. As the internal locking shaft 122 advances through the shaft spring collet 170, the flexible fingers 172 of the shaft spring collet 170 expand outwardly for engaging the internal walls of the bore 176 of the blocker 118. The outward expansion of the fingers 172 locks the blocker 118 to the distal end of the shaft 110.

Referring to FIGS. 12A and 12B, after the blocker 118 has been secured to the distal end of the shaft, one of the implant 174 may be secured to the distal end of the blocker 118. In one preferred embodiment, the blocker has a blocker spring collet 148 that is inserted into a bore 178 provided in the trailing end of the implant 174. As shown in FIG. 12B, the internal locking shaft 122 is advanced toward the distal end of the insertion tool so that the internal locking shaft 122 expands the flexible fingers 150 of the blocker spring collet 148. The outward expansion of the flexible fingers 150 secures the implant 148 to the blocker 118. The locking action is preferably obtained by the flexible fingers 150 engaging the inner wall surrounding bore 178. In preferred embodiments, the implant is secured to the blocker during insertion of the implant into an intervertebral disc space. After insertion of the implant into the disc space, the internal locking shaft 122 is retracted for releasing the implant from the blocker 118.

Figure 13A:
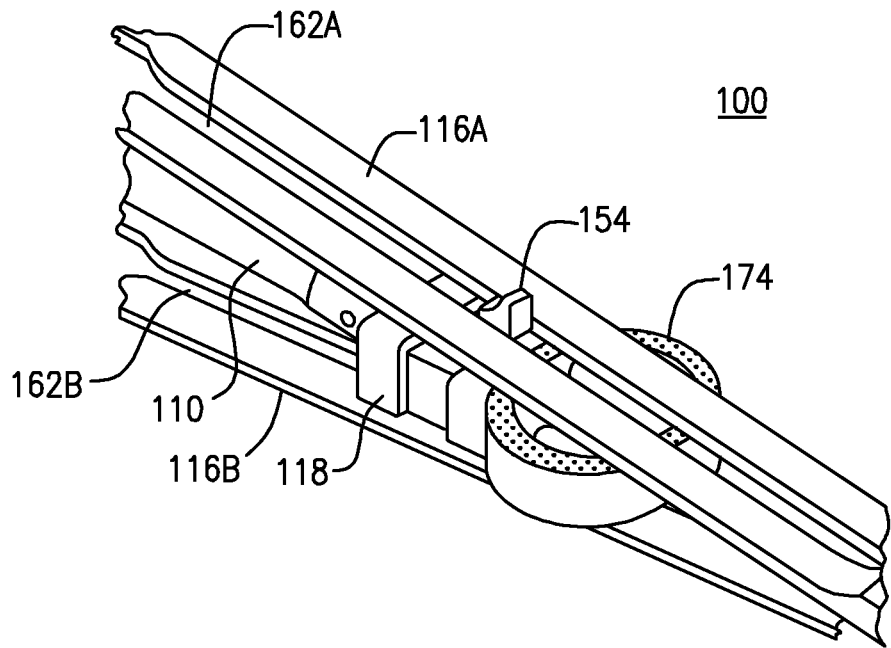
FIGS. 13A-13C show a method of advancing an implant toward a distal end of the insertion tool shown in FIGS. 1A and 1B, in accordance with certain preferred embodiments of the present invention.
Figure 13B:
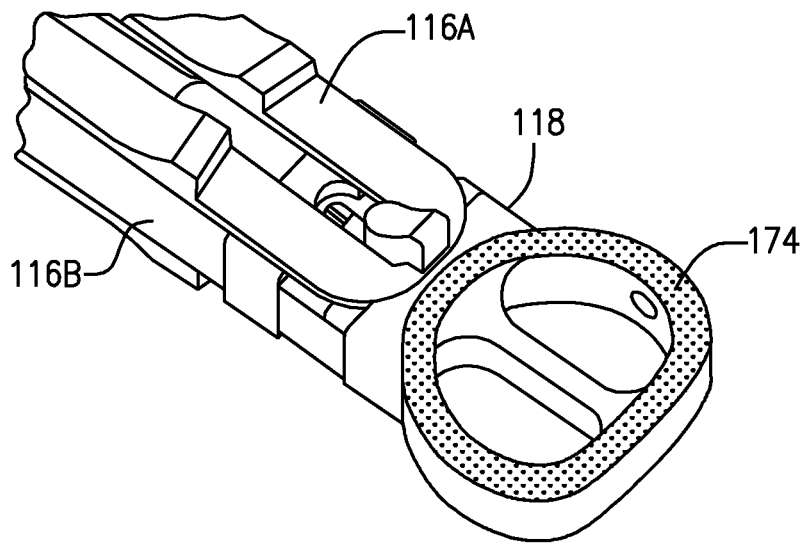
Figure 13C:
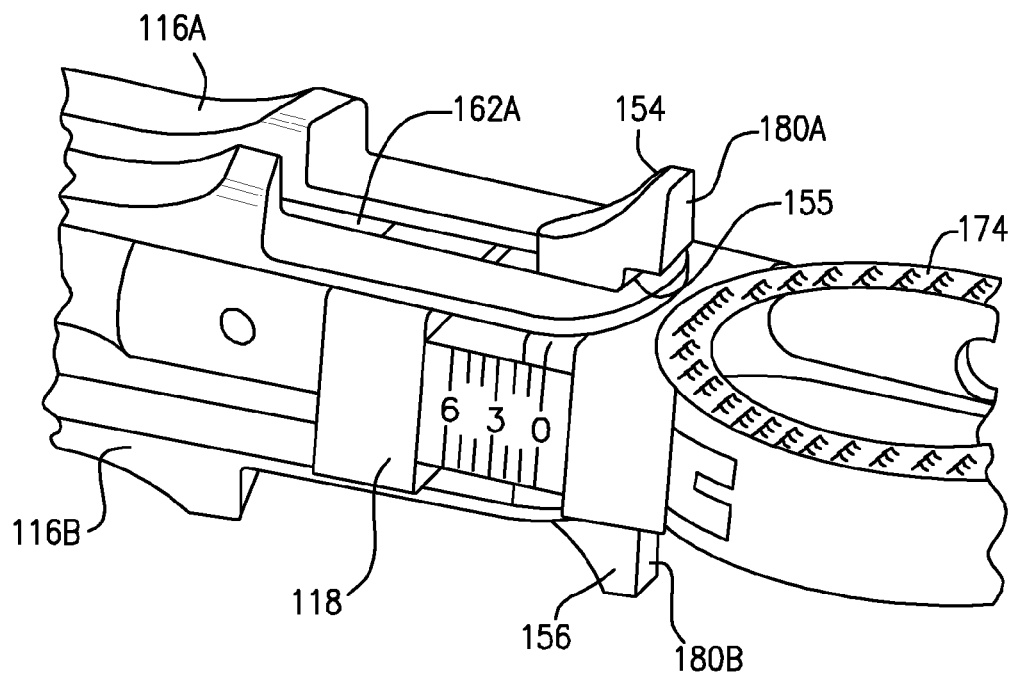

FIGS. 13A-13C show the insertion tool 100 after the blocker 118 has been secured to the distal end of shaft 110 and the implant 174 has been secured to the blocker 118.

As shown in FIG. 13A, the slots 162A, 162B provided in the respective guide rails 116A, 116B guide the blocker 118 and the implant 174 toward the distal end of the insertion tool 100. The first stop arm 154 on the blocker 188 slides through the first slot 162A for guiding advancement of the blocker 118 toward the distal end of the tool. Although not shown in FIG. 13A, a second stop arm (projecting from the bottom of the blocker) guides advancement of the blocker through the second slot 162B.

FIGS. 13B and 13C show the position of the implant 174 and the blocker 118 after the implant and blocker have been moved to the distal end of the first and second guide rails 116A, 116B. As shown in FIG. 13C, the first stop arm 154 has an undercut 155 that engages an end wall at the distal-most end of the first slot 162A. The second stop arm 156 also includes an undercut that engages an end wall at the distal-most end of the second slot (not shown). Each stop arm 154, 156 has a distal face 180A, 180B that is adapted to engage outer surfaces of vertebral bone. When the distal end faces 180A, 180B engage the vertebral bone, further distal advancement of the implant 174 into the disc space is halted.

Figure 14A:
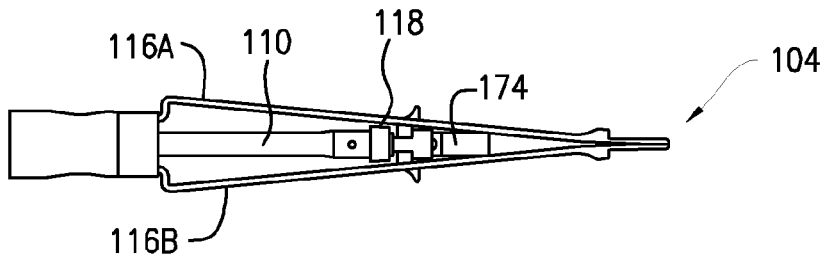
FIGS. 14A-14H show a method of inserting an implant between vertebrae, in accordance with certain preferred embodiments of the present invention.

Referring to FIGS. 14A-14H, in one preferred embodiment of the present invention, an implant 174 may be inserted into a disc space between vertebral bone. Referring to FIG. 14A, the implant 174 and the blocker 118 may be secured to a distal end of the shaft 110 using the structure and methods described above. As shown in FIG. 14A, the implant 174 and the blocker 118 are positioned between first guide rail 116A and second guide rail 116B. As the blocker 118 and the implant 174 are advanced toward the distal end 104 of the insertion instrument 100, the top and bottom surfaces of the blocker 118 engage the opposing inner surfaces of the first and second guide rails 116A, 116B. As a result, all of the forces required for separating the guide rails during a distraction operation are exerted upon the blocker 118 and not the implant 174. The blocker 118 thereby prevents the distraction forces from being exerted upon the implant 174, which may damage the implant.

Figure 14B:
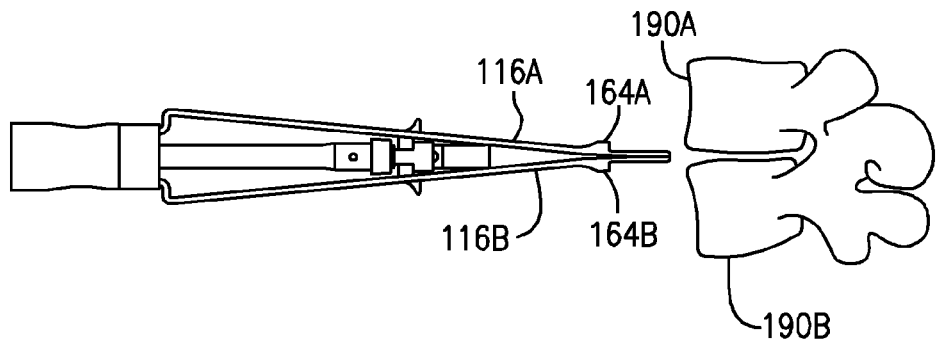
Figure 14C:
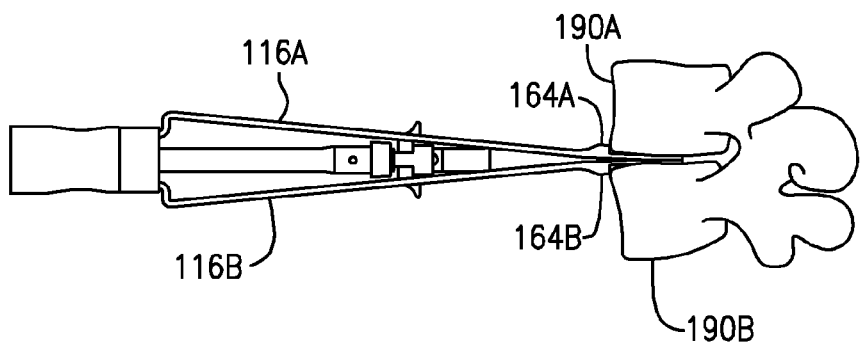

Referring to FIG. 14B, the distal ends of the respective guide rails 116A, 116B are inserted into a disc space between opposing vertebrae 190A, 190B. Referring to FIG. 14C, the guide rails 116A, 116B are advanced until the vertebral body stops 164A, 164B abut against outer surfaces of the opposing vertebrae 190A, 190B.

Figure 14D:
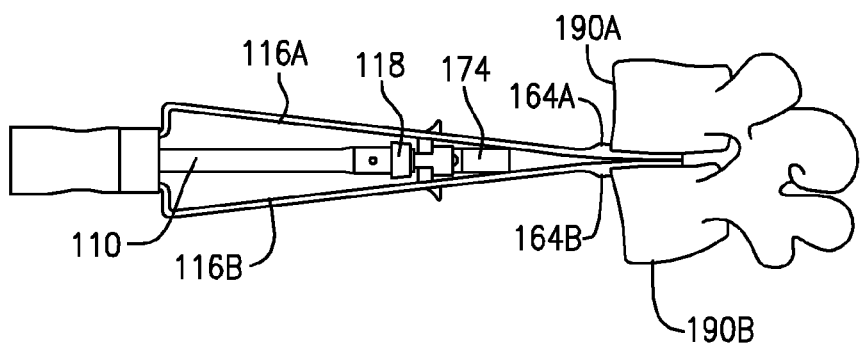

Referring to FIG. 14D, after the distal ends of the opposing rails 116A, 116B have been inserted between the vertebral bodies 190A, 190B, the shaft 110 is advanced toward the distal end of the insertion tool. The shaft may be advanced using the structure described above. As the shaft 110 advances toward the distal end of the insertion tool, the shaft 110 in turn urges the blocker 118 and the implant 174 toward the distal end of the insertion tool.

Figure 14E:
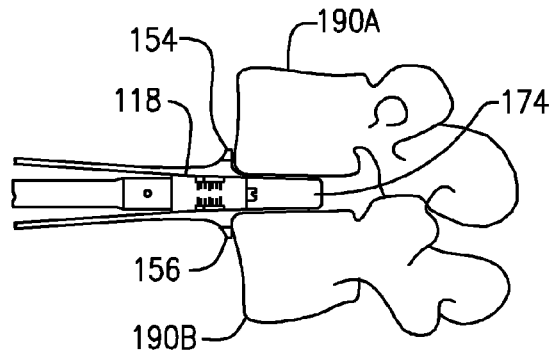

Referring to FIG. 14E, the blocker 118 provides the distraction force for distracting the disc space between the vertebrae 190A and 190B. The blocker 118 urges the implant 174 into the disc space until the distal faces of the stop arms 154, 156 abut against the outer surfaces of the vertebral bodies. At this point, the implant 174 has been fully inserted between the vertebral bodies.

Figure 14F:
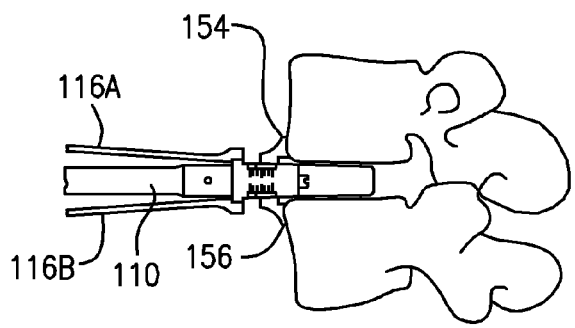
Figure 14G:
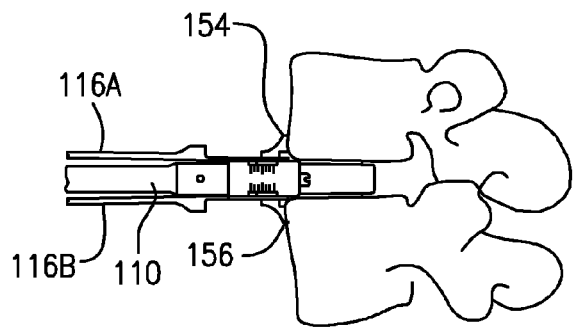
Figure 14H:
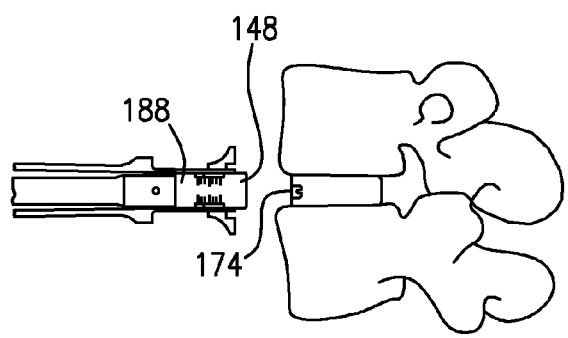

FIGS. 14F-14H show steps for retracting the distal ends of the guide rails 116A, 116B from their placement between the vertebral bodies. Referring to FIG. 14F, while pressing the stop arms 154 and 156 against the vertebral bodies, the guide rails 116A, 116B are retracted relative to the shaft 110. FIG. 14G shows further retraction of the guide rails 116A, 116B relative to the shaft 110. As the guide rails 116A, 116B are retracted relative to the shaft 110, the stop arms 154 and 156 remain pressed against the vertebral bodies.

Referring to FIG. 14H, the internal locking shaft (not shown) is retracted toward the proximal end of the tool so that the blocker 118 may be released from the implant 174. As the internal locking shaft is retracted, the resilient fingers on the blocker spring collet 148 are able to flex inwardly toward one another so as to release the implant 174 from the blocker 118.

Figure 15:
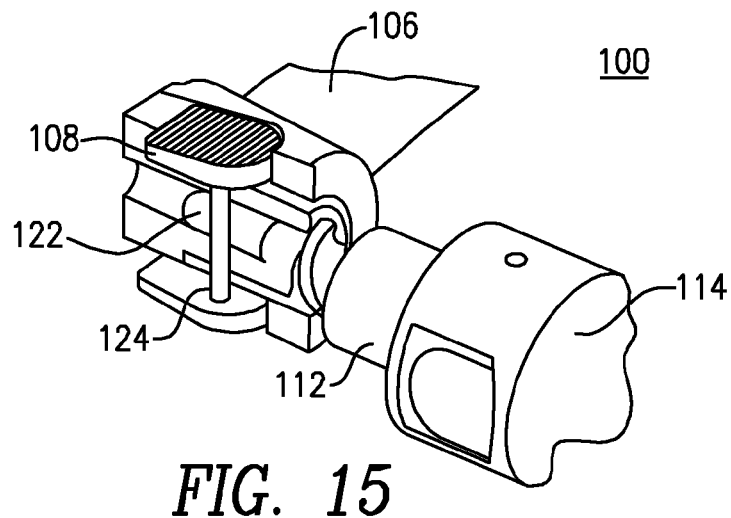
FIGS. 15 and 16A-16B show a method of unlocking an implant lock at a proximal end of the insertion tool shown in FIGS. 1A and 1B, in accordance with certain preferred embodiments of the present invention.
Figure 16A:
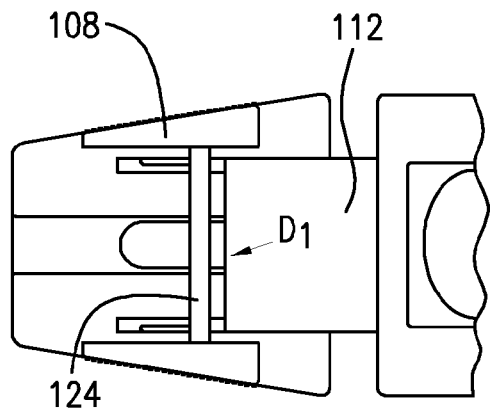
Figure 16B:
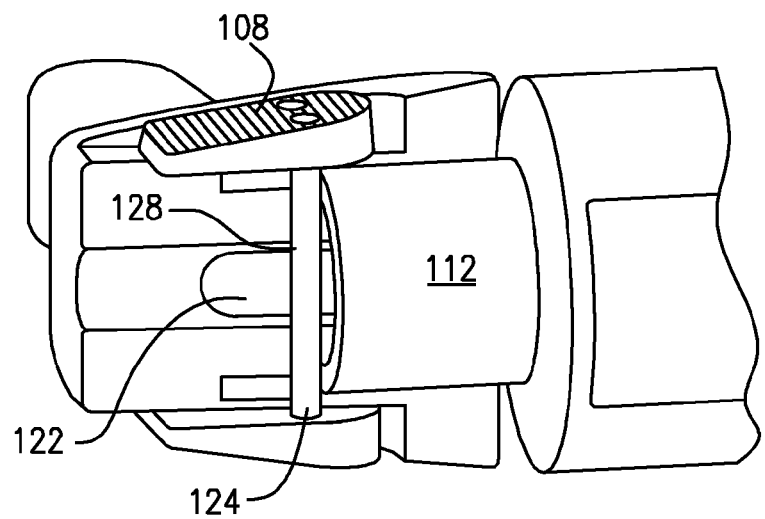

FIGS. 15-16B show a subassembly for automatically releasing the implant from the insertion tool, in accordance with certain preferred embodiments of the present invention. The subassembly includes a sleeve that may be retracted into the T-handle for engaging the implant lock and moving the implant lock into an unlocked position. As the implant lock is moved into an unlocked position, it in turn retracts the internal locking shaft for releasing an implant from the blocker.

Referring to FIG. 15, the insertion tool 100 includes the T-handle 106 mounted to the proximal end of the tool. The T-handle includes the implant lock 108 having pins 124 coupled with the proximal end of the internal locking shaft 122. In FIG. 15, the implant lock 108 is in the locked position. As a result, the internal locking shaft 122 is fully extended toward the distal end of the insertion tool 100 so that an implant may be secured to the tool. The insertion tool includes the sleeve 112 extending from a proximal end of the handle 114.

Referring to FIGS. 15 and 16A, as the T-handle 106 is rotated, the sleeve 112 moves toward the proximal end of the insertion tool in the direction $D_1$. As the sleeve 112 is retracted toward the T-handle, a leading edge of the sleeve 112 moves closer to the pins 124 of the implant lock 108.

Referring to FIG. 16B, further retraction of the sleeve 112 eventually results in the proximal end of the sleeve engaging the pins 124 and urging the pins 124 toward the proximal end of the insertion tool. This retracting movement causes the implant lock 108 to move from the locked position shown in FIG. 15 to the unlocked position shown in FIG. 16B. As the pins 124 move toward the proximal end of the insertion tool, the pins engage the undercut 128 in the internal locking shaft 122 for retracting the internal locking shaft 122 toward the proximal end of the insertion tool.

Figure 17A:
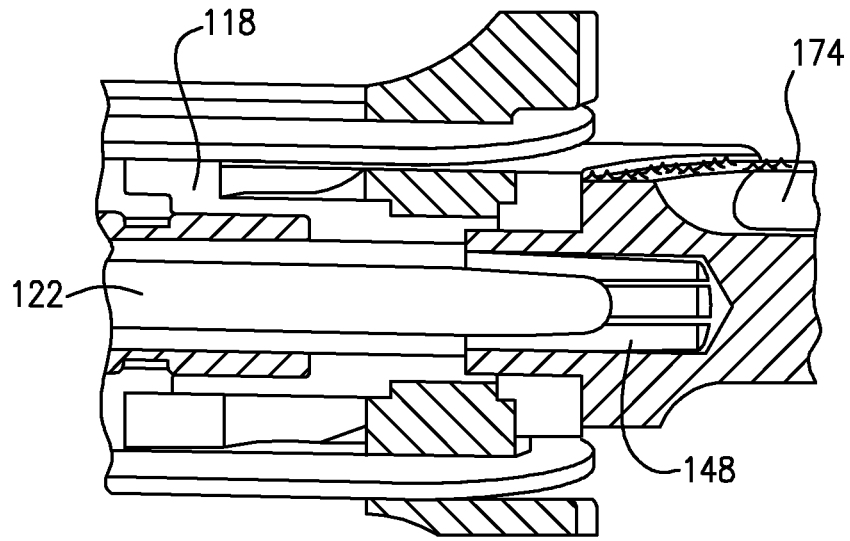
FIGS. 17A and 17B show a method of uncoupling an implant from a distal end of the insertion tool shown in FIGS. 1A and 1B, in accordance with certain preferred embodiments of the present invention.
Figure 17B:
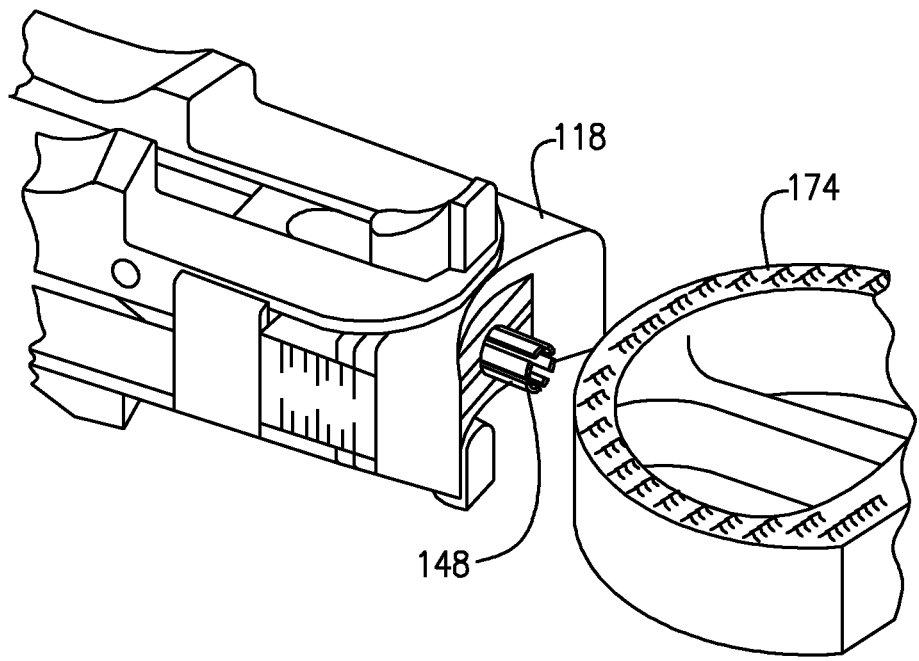

FIGS. 17A and 17B show the distal end of the insertion tool as the sleeve shown in FIG. 16B is retracted toward the proximal end of the insertion tool. Referring to FIGS. 16B and 17A, when the sleeve is retracted to the position shown in FIG. 16B, the implant lock 108 begins to urge the internal locking shaft 122 toward the proximal end of the tool. In response, as shown in FIG. 17A, the distal end of the internal locking shaft is retracted into the blocker 118. As the distal end of the internal locking shaft 122 is retracted, the flexible fingers of the blocker spring collet 148 are able to flex inwardly for releasing the implant 174 from the blocker 118.

FIG. 17B shows implant 174 after it has been detached from the blocker spring collet 148 at the distal end of blocker 118.

Figure 18A:
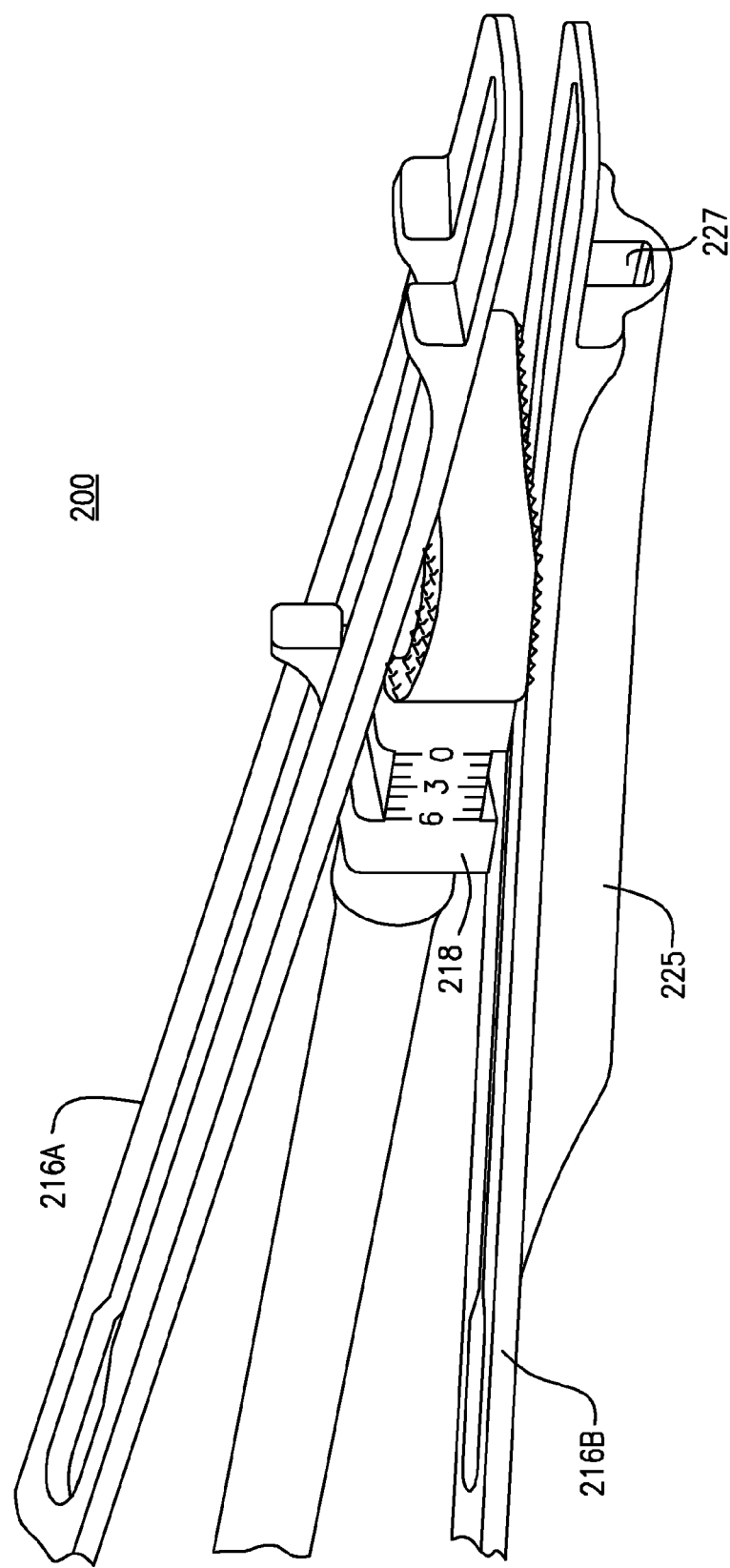
FIGS. 18A-18B show perspective views of an insertion tool for an intervertebral implant, in accordance with other preferred embodiments of the present invention.
Figure 18B:
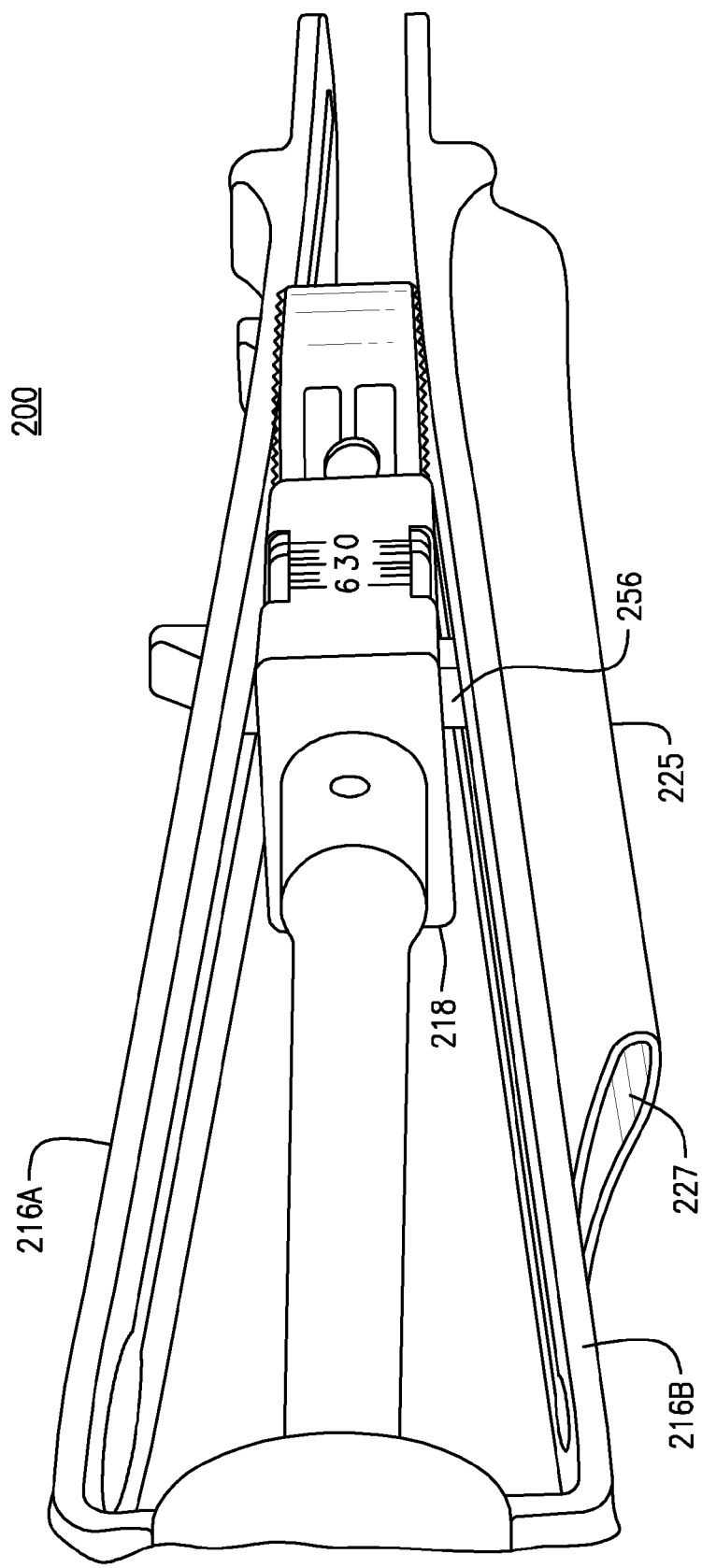

FIGS. 18A-18C show an insertion tool, in accordance with other preferred embodiments of the present invention. The insertion tool 200 includes first and second guide rails 216A, 216B for guiding an implant toward a distal end of the tool. In one preferred embodiment, the second guide rail 216B includes a protective hood 225 defining a channel 227 through which the second stop arm 256 on the blocker 218 is advanced toward the distal end of the tool. The protective hood 225 may have a curved exterior surface. The protective hood is desirably adapted for protecting nerves and soft tissue adjacent the spine as the implant is inserted between vertebrae. The protective hood may prevent the stop arms on the blocker from contacting the above-mentioned nerves and soft tissue. In certain preferred embodiments, the protective hood is only provided on one of the guide rails (e.g. either the first guide rail 216A or the second guide rail 216B). In other preferred embodiments, a protective hood may be provided on each of the guide rails.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of implanting an intervertebral implant comprising the steps of:

inserting a distal end of an intervertebral implant insertion instrument between two vertebrae, the implant insertion instrument including: a first handle having a first end and a second end; a second handle located towards the first end and connected to the first handle; a pair of rails attached to the second end of the first handle; and a shaft engaging the first handle and having a third end and a fourth end;

attaching a blocker to the fourth end of the shaft of the implant insertion instrument;

attaching an intervertebral implant to the blocker, the intervertebral implant having a top surface and a bottom surface;

adjusting the blocker along a proximal-distal axis of the implant insertion instrument to locate an end of the blocker at an offset distance from the two vertebrae;

sliding the intervertebral implant between the two vertebrae along a guide path on the implant insertion instrument without either the top surface or the bottom surface of the intervertebral implant being contacted by the implant insertion; and moving the first handle toward the second handle to automatically disengage the implant insertion instrument from the intervertebral implant.

2. The method of claim 1, further comprising selecting the blocker from a set of blockers, each blocker of the set having a differing height and being attachable to the fourth end of the shaft and an intervertebral implant.

3. The method of claim 1, wherein the guide path is defined by the pair of rails, and wherein the intervertebral implant is slid between the two vertebrae along the guide path without either the top surface or the bottom surface of the intervertebral implant being contacted by the pair of rails.

4. The method of claim 1, wherein the blocker has a spring collet with a plurality of fingers, and wherein the step of attaching the intervertebral implant to the blocker includes inserting the spring collet into an opening provided in the intervertebral implant, and opening the plurality of fingers.

5. The method of claim 1, wherein each rail defines a slot for slidably receiving at least one stop arm of the blocker therethrough, and wherein the step of sliding the intervertebral implant includes sliding the at least one stop arm within the corresponding slot to guide movement of the blocker along the guide path.

6. The method of claim 5, wherein the blocker is slid along the guide path until the at least one stop arm engages an end wall of the slot.

7. The method of claim 1, further comprising manually disengaging the first handle from the shaft to permit movement of the first handle in a proximal or distal direction along the shaft, wherein the step of attaching the intervertebral implant to the blocker further includes securing the intervertebral implant to the implant insertion instrument with a lock.

8. The instrument of claim 1, wherein the step of attaching the intervertebral implant to the blocker further includes securing the intervertebral implant to the implant insertion instrument with a lock, and further comprising moving the first handle toward the second handle to disengage the first handle from the shaft and move the lock into an unlocked position, wherein the first handle abuts the second handle to cause disengagement of the intervertebral implant.

9. The method of claim 1, further comprising the step of implanting the intervertebral implant between the two vertebrae.

10. A method of implanting an intervertebral implant comprising the steps of:
inserting a distal end of an intervertebral implant insertion instrument between two vertebrae, the implant insertion instrument including: a first handle having a first end and a second end; a second handle located towards the first end and connected to the first handle; a pair of rails attached to the second end of the first handle; and a shaft engaging the first handle, the shaft having a third end and a fourth end;
attaching a blocker to the fourth end of the shaft of the implant insertion instrument;
attaching an intervertebral implant to the blocker, the intervertebral implant having a top surface and a bottom surface;
securing the intervertebral implant to the blocker with a lock;
advancing the intervertebral implant between the two vertebrae along a guide path on the implant insertion instrument without either the top surface or the bottom surface of the intervertebral implant being contacted by the implant insertion instrument; and
unsecuring and releasing the intervertebral implant from the blocker by moving the first handle toward the second handle to automatically unsecure and release the intervertebral implant, wherein the first handle abuts the second handle to cause the release of the intervertebral implant from the blocker.

11. The method of claim 10, wherein the blocker has a spring collet with a plurality of fingers, and wherein the step of attaching the intervertebral implant to the blocker further includes inserting the spring collet of the blocker into an opening provided in the intervertebral implant.

12. The method of claim 11, wherein the step of attaching the intervertebral implant to the blocker further includes advancing a locking shaft into the spring collet so as to flex the plurality of fingers away from each other and adjusting the blocker to locate a proximal end of the blocker at an offset distance from the two vertebrae.

13. The method of claim 12, further comprising implanting the intervertebral implant between the two vertebrae.

14. A method of implanting an intervertebral implant comprising the steps of:
inserting a distal end of an intervertebral implant insertion instrument between two vertebrae, the implant insertion instrument including: a first handle having a first end and a second end; a second handle located towards the first end and connected to the first handle; a shaft threadably engaging the first handle, the shaft having a third end and a fourth end; and a pair of rails defining a guide path;
attaching a blocker to the fourth end of the shaft of the implant insertion instrument, wherein each rail has a slot adapted to slidably receive the blocker therein;
attaching an intervertebral implant to the blocker;
sliding at least one stop arm of the blocker within the corresponding slot to guide movement of the blocker along the guide path, wherein the at least one stop arm projects through the corresponding slot; advancing the intervertebral implant
between the two vertebrae along the guide path without engaging the implant with the pair of rails; and moving the first handle toward the second handle to automatically disengage the implant insertion instrument from the intervertebral implant.

15. The method of claim 14, wherein a distal portion of each rail of the pair of rails has a vertebral body stopper that prevents over-insertion of the pair of rails between the two vertebrae.

16. The method of claim 14, wherein the step of advancing the intervertebral implant further includes sliding the blocker along the guide path until the at least one stop arm engages an end wall of the slot.

17. The method of claim 14, further comprising selecting the blocker from a set of blockers, each blocker of the set having a differing height and being attachable to the fourth end of the shaft and an intervertebral implant.

18. The method of claim 17, further comprising implanting the intervertebral implant between the two vertebrae.

* * * * *